(12) United States Patent
Van De Stolpe et al.

(10) Patent No.: US 8,932,811 B2
(45) Date of Patent: Jan. 13, 2015

(54) GENOMIC SELECTION AND SEQUENCING USING ENCODED MICROCARRIERS

(75) Inventors: Anja Van De Stolpe, Eindhoven (NL); Jacob Marinus Jan Den Toonder, Eindhoven (NL); Pieter Jan Van Der Zaag, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/203,637

(22) PCT Filed: Feb. 26, 2010

(86) PCT No.: PCT/IB2010/050840
§ 371 (c)(1),
(2), (4) Date: Aug. 26, 2011

(87) PCT Pub. No.: WO2010/097775
PCT Pub. Date: Sep. 2, 2010

(65) Prior Publication Data
US 2011/0311975 A1   Dec. 22, 2011

(30) Foreign Application Priority Data
Feb. 27, 2009 (EP) .................................. 09153909

(51) Int. Cl.
| | | |
|---|---|---|
| C12Q 1/68 | (2006.01) | |
| C12P 19/34 | (2006.01) | |
| C12M 1/00 | (2006.01) | |
| C12M 1/34 | (2006.01) | |
| B32B 5/16 | (2006.01) | |
| C07H 21/02 | (2006.01) | |
| C07H 21/04 | (2006.01) | |

(52) U.S. Cl.
CPC .................................... *C12Q 1/6869* (2013.01)
USPC ....... 435/6.1; 435/6.12; 435/91.2; 435/283.1; 435/287.2; 428/402; 536/23.1; 536/24.3

(58) Field of Classification Search
USPC .................. 435/6.1, 6.12, 91.2, 283.1, 287.2; 428/402; 536/23.1, 24.3
See application file for complete search history.

(56) References Cited

U.S. PATENT DOCUMENTS

| | | | | |
|---|---|---|---|---|
| 6,934,408 | B2 * | 8/2005 | Frost et al. ..................... | 382/129 |
| 7,041,445 | B2 * | 5/2006 | Chenchik et al. ............. | 435/6.11 |
| 7,323,696 | B2 * | 1/2008 | Vann et al. .................. | 250/458.1 |
| 7,556,919 | B2 | 7/2009 | Chenchik | |
| 7,932,037 | B2 * | 4/2011 | Adler et al. .................. | 435/6.16 |
| 2005/0181440 | A1 | 8/2005 | Chee | |
| 2006/0275799 | A1 * | 12/2006 | Banerjee et al. ................... | 435/6 |
| 2008/0314749 | A1 | 12/2008 | Johnson | |
| 2009/0137053 | A1 | 5/2009 | Kishii | |

FOREIGN PATENT DOCUMENTS

| | | |
|---|---|---|
| EP | 1903337 A1 | 3/2008 |
| EP | 1995329 A2 | 11/2008 |
| WO | 9720073 A1 | 6/1997 |
| WO | 0063695 A1 | 10/2000 |
| WO | 0141931 A2 | 6/2001 |
| WO | 0233419 A1 | 4/2002 |
| WO | 03035229 A2 | 5/2003 |
| WO | 2004070362 A1 | 8/2004 |
| WO | WO 2007/084702 * | 7/2007 |
| WO | 2007115815 A1 | 10/2007 |

OTHER PUBLICATIONS

Blast Datasheet 1 target sequence [down loaded from the internet: http://blst.ncbi.nlm.nih.gov/Blast], printed on Sep. 20, 2012, pp. 1-5.*
Blast Datasheet 3 target sequence [down loaded from the internet: http://blst.ncbi.nlm.nih.gov/Blast], printed on Sep. 20, 2012, pp. 1 and 2.*
Huang et al, A Method for Generation of Arbitrary Peptide Libraries Using Genomic DNA, 2005, Molecular Biotechnology, 30, 135-142.*
Hodges, Emily et al "Genome-Wide in situ Exon Capture for Selective Resequencing" Technical Reports, Nature Genetics, vol. 39, No. 12, Dec. 2007, p. 1522-1527.
Braeckmans, Kevin et al "Encoding Microcarriers by Spatial Selective Photobleaching" Nature Materials, vol. 2, No. 3, Mar. 2003, pp. 169-173.
Jain, K.K. "Nanodiagnostics: Application of Nanotechnology in Molecular Diagnostics" Expert Review of Molecular Diagnostics, Future Drugs, vol. 3, No. 2, Jan. 2003, pp. 153-161.
Braeckmans, Kevin et al "Encoding Microcarriers: Present and Future Technologies" Nature Reviews, Drug Discovery, vol. 1, No. 6, Jun. 2002, pp. 447-456.

* cited by examiner

*Primary Examiner* — Narayan Bhat

(57) ABSTRACT

The present invention relates to a method for determining the sequence of a nucleic molecule. Herein a capture oligonucleotide probe is attached to an encoded microcarrier, wherein the code of said microcarrier identifies the sequence of said oligonucleotide probe. The capture oligonucleotide probe is hybridized with a sample comprising nucleic acids molecules, wherein said DNA fragment comprises a sequence which is complementary to the sequence of the capture oligonucleotide probe. The sequence of the DNA molecule is determined, wherein the capture oligonucleotide probe serves as a primer for a DNA polymerase, in the case of single molecule sequencing this is a sequencing primer. After the sequence determination, the nucleotide sequence of the capture oligonucleotide probe is identified by determining the code on the microcarrier, which corresponds with the capture oligonucleotide probe. This sequence information directly identifies the location of the sequenced DNA fragment on the genome, allowing direct comparison.

16 Claims, 1 Drawing Sheet

GENOMIC SELECTION AND SEQUENCING USING ENCODED MICROCARRIERS

FIELD OF THE INVENTION

The present invention relates to nucleic acid hybridization and sequencing methods. The present invention further relates to the selection, sequencing and identification of nucleic acid fragments using encoded microcarriers.

BACKGROUND OF THE INVENTION

Recent sequencing techniques allow the simultaneous determination of large quantities of nucleotide sequences. This abolishes the need to perform separate sequencing reactions in different capillaries or separated reaction wells. Typically, a DNA sample is fragmented by mechanical or enzymatic techniques, after which individual DNA fragments are bound to a substrate (e.g. the wall of a reaction chamber or a microcarrier/bead) via one type of nucleotide linker molecule attached to the fragment, which also functions as a universal primer. For technologies other than single molecule sequencing, a PCR-based amplification step follows. For example, sequencing techniques such as "454" pyrosequencing (Roche) use individual microbeads as a substrate, which are arranged in microwells of a reaction chamber. Subsequently in all techniques, nucleotides are stepwise incorporated and identified for each DNA molecule bound to the substrate. This process is repeated a number of times and the sequencing reads of all the individual fragments are aligned to get the complete sequence of a target DNA sample under investigation. These techniques are known in the art as "next generation sequencing" and are commercialized by companies such as Helicos, Illumina and Applied Biosystems and Roche. Next generation sequencing methods require that the different reactions, which are performed at the same time, can be physically separated from each other.

Enrichment of a DNA sample can be performed prior to sequencing in order to reduce the complexity of the sample and select specific areas of the genome for sequencing. Methods are described in Hodges et al. (2007) *Nature Genetics* 39, 1522-1527 to select or enrich genomic DNA fragments for subsequent sequencing by the choice of hybridization probes. More versatile methods for DNA hybridization have been developed wherein multiplexing methods are performed partially or entirely in solution and wherein the individual reactions are indexed using microcarriers with different colors or using encoded markers (reviewed in Braeckmans et al. (2002) *Nature Rev. Drug Discovery* 1, 447-448). In this context, Braeckmans et al. (2003) *Nature Mat.* 2, 169-173, suggest the use of photobleached encoded particles for DNA hybridization assays.

A drawback of current sequencing methods is the comparatively short individual read length of DNA that can be sequenced, leading to sequences that have limited information content. This makes it often difficult to position a determined sequence in a reference genome sequence (annotation of sequences). This is especially difficult in the case of bisulfate sequencing, where prior to the sequencing reaction unmethylated C nucleotides within CpG sequences in a fragment are converted to T nucleotides, resulting in reduced information for alignment of sequencing reads with the reference genome and consequently increased difficulty in correct assembly of the final nucleic acid sequence. Especially for future clinical diagnostic applications such as cancer sequencing, microbiology and clinical genetics, it would be advantageous to speed up the time needed to determine the sequence of a patient genomic sample, and obtain the highest possible accuracy.

SUMMARY OF THE INVENTION

Particular and preferred aspects of the invention are set out in the accompanying independent and dependent claims. Features from the dependent claims may be combined with features of the independent claims and with features of other dependent claims as appropriate and not merely as explicitly set out in the claims.

The present invention relates to a method for determining the sequence of a target nucleic acid molecule comprising the steps of:

a) providing a capture oligonucleotide probe attached to an encoded microcarrier, wherein the code of said microcarrier identifies the sequence of said oligonucleotide probe and/or its location on a reference genome, b) hybridizing said capture oligonucleotide probe with a sample comprising a nucleic acid molecule, wherein said nucleic acid molecule comprises a sequence which is at least partially complementary to the sequence of the capture oligonucleotide probe, c) determining the sequence of the hybridized nucleic acid molecule of step b) by generating a sequence read of at least 2 nucleotides, d) determining the code on the microcarrier, e) identifying the nucleotide sequence of the capture oligonucleotide probe corresponding with the code on the microcarrier and/or its location of the reference genome as determined in step d), f) combining the sequence information determined in step c) with the information identified in step e) to determine the sequence of a target nucleic acid molecule.

Steps c and d can be performed in any order.

Current methods known in the art comprise the step of binding a selected fraction of a DNA sample to a set of probes. The information of which individual DNA fragment hybridized with each of the probes on the array gets lost as all hybridized DNA fragments are released from the array and processed in bulk in further sequencing steps.

The above identified problem is solved by the method according to the invention. The present invention results in an increase in the information content of a determined sequence while at the same time exploiting the advantages of the recently developed DNA sequencing techniques, such as the large throughput and speed and sensitivity. The present invention elegantly shows integration of genome enrichment/selection and sequencing steps, providing minimized assay time and sample loss, and thereby improved specificity of the diagnostic sequencing test. The method facilitates determining sequence alterations of the target nucleic acid molecule as compared to the reference sequence.

In a preferred embodiment, the target nucleic acid molecule comprises at least 2 nucleic acid probe sequences.

A further embodiment of the present invention is a device for determining the sequence of a nucleic acid sample, said device comprising a unit for annealing capture probes with nucleic acids, a unit for determining the sequence of a DNA molecule, a unit for manipulating a microcarrier and a unit for determining the code of a microcarrier.

In particular embodiments of the methods of the present invention, a plurality of differently encoded microcarriers is used, wherein each code corresponds with a unique sequence of a capture oligonucleotide probe. Preferably, the encoded microcarrier is in suspension during one or more steps of said method.

In other particular embodiments of the methods of the present invention, the microcarrier is a magnetic particle or a charged particle.

Optionally, in step d) the carrier is positioned in a magnetic field.

In particular embodiments of the methods of the present invention, in step d) the code of the encoded carrier is determined with optical methods.

The microcarrier can be a fluorescent particle wherein the code is applied by photobleaching.

Sequence determination can be performed for example by determining the fluorescence resonance energy transfer (FRET) of incorporated fluorescent nucleotides, but multiple other known sequencing chemistries are usable.

In particular embodiments of the methods of the present invention, the length of the sequence determined in step c) may have a length between 20 and 40 nucleotides.

DNA samples as used in the present invention can be generated by fragmenting genomic DNA, for example with a restriction enzyme. Using such fragmenting methods, the average length of the fragmented DNA can be chosen by selecting specific restriction enzymes. The preferred length is between 200 and 1000 base pairs.

Another aspect of the present invention relates to a device for determining the sequence of a nucleic sample, said device comprising a unit for annealing capture probes with nucleic acids, a unit for determining the sequence of a DNA molecule, a unit for manipulating a microcarrier and a unit for determining the code of a microcarrier.

Such device can be a microfluidic device. In particular embodiments, the unit for manipulating a microcarrier comprises a means for applying at least one magnetic field.

Methods and devices in accordance with the present invention dramatically increase the information content of a sequenced DNA fragment. In the prior art, linker DNA sequences were used to randomly immobilize DNA fragments to a substrate. In the present invention DNA fragments are immobilized to a microcarrier via hybridization to a complementary DNA oligonucleotide probe (capture probe). The microcarrier which is used is encoded to identify the sequence of the capture probe. In the methods of the present invention the capture probe functions to specifically extract a DNA fragment from whole genome DNA similar to microarray-based genomic selection (MGS) technologies. The capture probe optionally further functions as a primer for DNA polymerase based DNA amplification (PCR-cloning step) or single molecule sequencing methods. Herein preferably only one DNA fragment is bound to one microcarrier. The information of the hybridized (captured) DNA fragment, or after the sequencing step, the information of the sequenced fragment is combined with the information of the capture probe by determining the corresponding code on the microcarrier. The use of encoded microcarriers allows performing all or part of the reaction steps and manipulations in solution. The increase in sequence information that is obtained by both the sequence from the capture probe and the determined sequence, will dramatically reduce the time for sequence assembly and will require less complicated software and hardware.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1A:
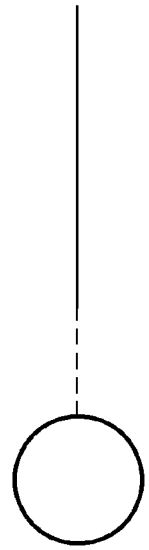
FIG. 1 schematically compares a prior art hybridization method (A) with a hybridization method (B) in accordance with an embodiment of the present invention.

A: A DNA fragment (solid line) is ligated to a linker (dashed line) attached to a microcarrier without code.

B: A DNA fragment (solid line) hybridized with a capture probe (dotted line) attached to an encoded microcarrier.

DETAILED DESCRIPTION OF THE INVENTION

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art.

"(Micro)carrier" as used in the present invention relates to a particle, preferably a solid particle, with a diameter of between 0.1 and 1000 micrometer. Synonyms are "(micro)bead", "(micro)particle" or "(micro)sphere" or "nanostring". The shape of the microbeads is not considered as a limitation of the invention.

"Capture probe" as used in the present invention relates to an oligonucleotide molecule (or part thereof) which binds specifically to a complementary nucleotide sequence.

"Encoded" as used in the present invention relates to a detectable property (e.g. color, patterning, alphanumeric information) of a microcarrier, which allows discriminating one microcarrier from another one. In its most simple meaning it refers to the discrimination between two microcarriers.

"Code" as used in the present invention refers to a device-readable code on microcarrier, ensuring a complexity of at least 100, 250, 500, 1.000 2500, 5000 or 10.000. The DNA sequence which is determined by polymerase dependent nucleotide incorporation or ligase dependent oligomer addition is also referred to as "sequence read".

The nucleic acid is typically DNA, but the methods are also applicable to RNA (such as messenger RNA (mRNA) or microRNA, which also hybridizes to oligonucleotide capture probes and which may be converted into DNA using reverse transcriptase based methods.

In these methods, the capture oligonucleotide probe can serve in step c) as a sequencing primer for a DNA polymerase.

The present invention relates to hybridization and DNA sequencing methods. Methods in accordance with the present invention are applicable in any sequencing approach, including conformation sequencing of genomes to determine genetic variety between strains and races of a species, or de novo sequencing of genomes. A particular embodiment refers to the sequencing of individual mammalian (in particular human) genomes to identify SNPs in an individual.

Sample and Fragmentation of Nucleic Acid

Selected parts of whole genome DNA can be sequenced by using the methods of the present invention. Alternatively, samples are partially purified by e.g. isolating individual chromosomes or isolating fragments via e.g. pulsed field electrophoresis.

Genomic DNA is fragmented to the chosen length prior to incubation with the microcarriers. The sample genomic DNA is usually fragmented using standard technology, delivering fragments in the chosen range of 80-1000 nucleotides, however the preferred length depends on the chosen length of the capture probes, and usually is longer than the length of the capture probes.

Fragments can be obtained using physical methods (e.g. sonication, physical shearing). DNA fragments can also be obtained using restriction enzymes (or combinations of different restriction enzymes), which give predictable and reproducible mixtures of fragments of a defined length. The average length of fragments can be tailored by choosing enzymes which have either short recognition sites (resulting in a large number of short fragments) or long recognition sites (resulting in a smaller number of longer fragments), or a combination.

When a whole genome DNA sample with known reference genome sequence is used, the use of restriction enzymes allows the exact prediction of the length of a fragment and the sequence at the ends of a fragment. This allows to predict at which position in a fragment a capture probe will hybridize, and consequently to predict the length of non-hybridized sequence at the 3' and 5' end of the hybridized probe, of which the part at the 3' end of the probe can be sequenced to produce a sequence read.

Alternatively, RNA can be used as sample. RNA can be converted into DNA using reverse transcriptase based methods. After the conversion the sample can be processed as any other DNA sequence.

Microcarriers

Microcarriers used in the present invention are made of a material or functionalized with a material which allows the binding of oligonucleotides "capture probes" to the microcarrier. The coupling of oligonucleotides to microcarriers is well known in the art. This coupling can be irreversible or reversible (e.g. by thiol, acid, or alkali labile groups).

In methods in accordance with the present invention, (and this in contrast to microarray techniques), a capture probe is not identified by its co-ordinates on a matrix but is identified by the code or the nature of the microcarrier. As a consequence, encoded microcarriers with capture probes can be present in solution in at least one step or even in all steps of the described methods. Microcarriers as used in the present invention can vary in shape, size, porosity, material and other features, depending on the particular requirements of the assay or device wherein sequencing methods in accordance with the present method are performed. Methods as described in the present invention can be performed in existing sequencing apparatus without or with minimal adaptations. Accordingly microcarriers with a diameter of about 1 µm or about 40 µm are suitable in respectively ABI solid sequencing and '454' sequencing.

In certain embodiments the particles have a size and shape that allows the manipulation of particles in a microfluidic device. Microcarriers may have an electric charge to allow the manipulation in an electric field.

In other embodiments the carriers are magnetic or magnetizable particles, which allows the manipulation, rotation or positioning in a magnetic field.

In other embodiment the particles are positioned and or manipulated using optical tweezers.

Microcarriers as used in the present invention further comprise a code, which allows the identification of an individual carrier within a plurality of carriers. The encoding of carriers has been known for a long time in multiplexing methods wherein carriers are functionalized with chromophoric (e.g. fluorescent) labels with different absorption or emission maxima. For example Luminex (Austin, Tex.) provides microcarriers, comprising different concentrations of two dyes resulting in 100 different blends.

A higher complexity of encoding is achieved by using e.g. quantum dots, allowing a complexity of up to 1 million using 10 intensity levels and 6 colors.

In particular embodiments a high complexity is obtained by using non-chromophoric barcode methods allowing a complexity of more than 100,000, more than 1 million or even up to 10 or 100 million.

Different type of barcodes are known in the art and include electronic barcode using radio frequency tags, laser etched barcodes, metallic nanorods (reviewed in Jain K. (2003) *Expert Rev Mol Diagn.* 3, 153-161; Lehmann (2002) *Nature Materials* 1, 12-13; Braeckmans et al. (2002) *Nature review, drug discovery* 1, 447-448). In metallic nanorods, the barcode is obtained by the different materials, which are used to make the carriers.

In particular embodiments, the barcode is a miniaturized readable code of any geometry, design, or symbol that can be written on the surface or even within and read on the microcarriers. For example, the codes may be written as numbers or letters, or as codes in the form of symbols, pictures, bar codes, ring codes, or three-dimensional codes. Ring codes are similar to bar codes, except that concentric circles are used rather than straight lines. Alternatively two-dimensional patterns are used to represent a code.

In a particular embodiment a high complexity is obtained using barcodes which are written on or within a microcarrier via partial photobleaching of fluorescent particles. This process allows writing symbols, lines, numbers and the like on particles. A line pattern can be written on a microcarrier such that a barcode pattern is obtained that can be read by optical devices. The spatial selective photobleaching of microcarriers is described in detail in Braeckmans et al. (2003) *Nature Materials* 2, 169-173 and Serveaux (2007) *Langmuir.* 25 10272-10279. A barcode can be written several times on a microcarrier, allowing to read the barcode irrespective of the orientation of the microcarrier.

In a further particular embodiment the microcarrier comprises also magnetic material, which allows magnetic manipulation of the particles. The manufacture of such particles is described in detail in patent applications WO2007115815, EP1346224 and WO0063695.

Enrichment and Hybridization

The sequence of the oligonucleotide is chosen based on the reference genome (in case of a human sample, the human genome), with the purpose of enabling the capture of a DNA fragment from a fragmented whole genome DNA sample.

The captured fragment comes from the same genomic location as the capture probe, such that a sequence 3' from the capture probe can be sequenced using the captured DNA fragment as template. Identifying the code on the microcarrier subsequently allows the identification of the capture probe and the correlated genomic location of the DNA fragment bound to the capture probe, without the need to determine the sequence of this oligonucleotide itself. This allows direct comparison between the sequenced part of the captured DNA fragment with the reference genomic sequence from the human genome (or any other reference genome if the sample is from a non human origin).

The methods of the present invention comprise the step of hybridizing a DNA sample comprising a fragmented genome, with a plurality of different oligonucleotide capture probes, wherein multiple identical capture probes are attached to a single encoded microcarrier. According to one embodiment, oligonucleotides are designed based upon a known reference sequence, in order to cover a region of a chromosome, an entire chromosome or even the entire genome of an organism. In particular applications the oligonucleotides are designed to hybridize at a defined distance from the cleavage site of the restriction enzyme that was used to fragment the sample. In this embodiment, not only the determined sequence of a thus captured DNA fragment but also the length of the sequence that is determined until the end of the fragment is reached can be predicted, thus providing information about the position of the determined sequence in a reference genomic sequence.

Alternatively a library of oligonucleotides is used, irrespective of the DNA sequence of the investigated DNA sample. Regardless of the approach, precautions are taken during the design of a set of probes that such a set does not comprise probe pairs which are complementary to each other.

For example, microcarriers are manipulated and positioned temporarily on a surface during the denaturing and subsequent annealing with DNA fragments such that hybridization between two complementary probes is not possible.

Alternatively different limited sets of probes are generated which do not hybridize pairwise. The hybridization with the fragmented DNA is performed with a first set of probes on encoded microcarriers (enrichment of DNA fragments of choice). After the separation of the bound and unbound DNA, the unbound DNA is hybridized again with a second set of probes on similarly encoded microcarriers. This process can be repeated until all probes have hybridized with the corresponding DNA fragment in the sample. After the hybridization, all hybridized sample DNA fragments can be pooled together and further processed in parallel.

In the methods of the present invention, the possibility exists that two (or more) different probes hybridize at difference positions at a single DNA fragment when a large collection of different probes is hybridized with a DNA sample. In this situation, a DNA fragment will carry two (or more) different codes and subsequent sequencing of such a particle will generate a multiple signal. The chance of different probes binding to the same DNA fragment can be minimized by increasing the length of the probes and/or by decreasing the average length of the DNA fragments, using different restriction enzymes or shearing conditions.

The capture probe can be of varying length, in general longer than the length used for so-called array-based sequencing, where sequencing is based on differential hybridization of a DNA fragment, which will preferentially bind to the completely homologous hybridization probe. The longer capture probe facilitates capture DNA fragments by means of partial hybridization, where mismatches between capture probe and DNA fragment are allowed, but irrelevant for the sequencing read.

The length of the capture oligonucleotide hybridizing with the DNA can range from about 15 up to 30, 40, 60, 75, 90 or 150 or 200 nucleotides. The capture probes are preferably over 40 nucleotides long. In addition to the hybridizing part of the oligonucleotide, the capture probe can comprise additional oligonucleotides or other molecule(s) which function as a spacer between the microcarrier and the hybridizing part. The longer the hybridizing part of a probe, the less frequent a complementary sequence occurs in a sample, but the more selective the capture of DNA fragments will be, while at the same time allowing mismatches, due to unknown mutations (especially in a cancer genome sample) to be present and not interfere with the capture.

The capture probe can be bound both 5' and 3' to the microcarrier surface, however if the choice is for a subsequent polymerase amplification reaction or sequencing reaction by synthesis, using the capture probe as primer, and using a polymerase, the capture probe is coupled to the microcarrier surface with the 5' end.

The microcarriers with coupled capture oligo's are incubated according to a standard protocol used for genome enrichment with the fragmented DNA sample, as described, during sufficient time (e.g. 3 days, preferably 24 hours, even more preferably under 180 minutes) to specifically capture a sufficient number of DNA fragments by specific hybridization to the capture probes.

In one embodiment this hybridization phase occurs in a micro fluidics device where hybridization kinetics are optimized, and required time for optimal capture is reduced.

The chance of different probes binding to the same DNA fragment can be minimized by increasing the length of the probes and/or by decreasing the average length of the DNA fragments, using different restriction enzymes or shearing conditions.

The ratio between fragment and probe is flexible, depending on the way of sequencing the captured fragment. In case of directly sequencing multiple of the captured fragments with the same type of capture probe as primer on one carrier, the occupancy of the capture probes needs to be high, close to 1:1 or 1:2. This is necessary to increase the signal during the sequencing reaction.

This in contrast to when a PCR step in between is involved to amplify the captured fragment. In the case of direct single molecule sequencing the captured fragments should be sufficiently separated to enable detection of individual molecule sequencing reactions, for example one captured fragment on a single microcarrier.

Upon hybridization, reaction conditions, concentration of DNA sample and oligonucleotide capture probes are chosen to obtain the desired probe occupancy, for example high occupancy, or low occupancy per micro carrier.

In one embodiment reaction conditions, concentration of DNA sample and oligonucleotide capture probes are chosen such that statistically only one DNA fragment binds to a microcarrier with a probe because a microcarrier will typically carry a plurality of identical probes on its surface. Alternatively, the manufacture of the microcarriers is modified in order to have a maximum of one probe per microcarrier. After hybridization, unbound DNA can be removed by manipulating the encoded microbeads out of the hybridization reaction chamber, or by immobilizing the microcarriers to a position in the reaction chamber, whereafter one or more washing steps are performed to remove unbound DNA.

In certain embodiments the population of microcarriers can be sorted and identical carriers, with the same code, can be pooled. At this stage, the hybridized DNA may remain attached to the probe and the microcarrier and processed together in the remainder of the method. In an alternative approach, the hybridized DNA can remain attached to the probe while the probe is released from the microcarrier, e.g. by reducing a disulfide bridge linking the probe to the carrier.

After release of the captured DNA fragments from one group of identical carriers with the same code, the knowledge on their genomic position is retained. Sequencing this selected pool of fragments will reveal a DNA read of which the location on the genome is known. The same sorting and pooling procedure can be used for all other groups of microcarriers with specific codes.

Sequencing Reaction

The following step of the described methods comprises determining the sequence of a single DNA fragment that has hybridized to a capture probe. Herein, the same oligonucleotide that has been used in the hybridization process as capture probe optionally functions as a sequencing primer. After the incorporation of one or more nucleotides during the sequencing process, the incorporated sequence is determined and the code on the microcarriers is determined.

Single Molecule Sequencing

In one embodiment the captured fragments are directly and individually sequenced after capture. A particularly appropriate chemistry for single molecule sequencing approaches is using fluorescent labeled nucleotides using FRET (such as e.g. commercialized by Visigen). Herein an engineered DNA polymerase contains a donor fluorophore, and one of four differently colored acceptor fluorophores is attached to the gamma phosphate of each of the nucleotides. When a nucleotide is incorporated, the proximity causes a FRET signal. The DNA molecule lights up and the color indicates the base identity because the fluorophores on the nucleotides are color-coded. Each time a nucleotide is incorporated, the pyrophosphate containing the fluorophore is released so that the nascent strand synthesized is natural DNA, and no additional processing is needed before the next nucleotide can be incorporated. Optical detection here detects incorporation of nucleotides per captured DNA fragment.

In an alternative particular embodiment a reversible dye terminator method is used as described in Ju et al. (2006) *Proc Natl. Acad. Sci.* 103, 19635-19640. Contrary to conventional sequencing methods, only terminator nucleotides are used, each having a different fluorescent label, such that only one nucleotide can be incorporated by a DNA polymerase. The nature of the incorporated nucleotide is determined and the terminator group and the fluorescent group are removed. Hereafter, a further sequencing step can be performed.

Direct Sequencing

In one embodiment the captured fragments are directly sequenced after capture, and the combined signal optically detected. Here, sufficient captured fragments are present to enable detection of incorporation of each nucleotide during the sequencing reaction, where the signal is made up of the simultaneous sequencing reactions occurring from multiple capture probes on one microcarrier. This is most suited for sequencing of a non-cancer genomic DNA sample, like for clinical genetics diagnostics, where a maximum of two alleles in the DNA fragment mix is expected.

Emulsion Based

In particular embodiments, encoded microcarriers are present during one or more steps within an emulsion that functions as a reaction chamber (picoreactor) reaction, e.g. for performing PCR based amplification reactions. In these emulsion droplet amplification methods the microcarrier remains present in order to retain the sequence information of the capture probe. Equally, in those applications where DNA is removed from a microcarrier, the microcarrier remains in the same emulsion droplet/microwell to avoid that the encoded information on the microcarrier becomes lost. The encoded microcarriers with capture probes are mixed with genomic DNA fragments in oil to produce an emulsion. The concentration of the different components is chosen such that a single encoded microcarrier with capture probe(s) and a single DNA fragment and amplification reagents end up together in every emulsion droplet picoreactor in the emulsion. When magnetic particles are used, its magnetic properties can be used to transport and manipulate the droplets of the emulsion and to align the particles. Beads can be individually manipulated using their magnetic capacity and micro fluidics to transport them. In this situation, in subsequent steps amplification and sequencing ingredients can be added. Herein beads are separated and immobilized from each other to such extent that individual microcarrier sequencing reactions can be detected. Generally the temperature is kept low to prevent the sequencing action to start until ready for detection. The emulsion droplets are aligned in a row or grid whereafter the sequencing reaction starts in one droplet, followed by the next droplet, by increasing the temperature to start the polymerase. Multiple detectors can be used in this way in a high throughput approach.

Generally in a sequencing reaction, the encoded microcarriers with capture probes are mixed with genomic DNA fragments in oil to produce an emulsion. The concentration of the different components is chosen such that a single encoded microcarrier with capture probe and a single DNA fragment and amplification reagents end up together in every emulsion droplet picoreactor in the emulsion. When magnetic particles are used, its magnetic properties can be used to transport and manipulate the droplets of the emulsion and to align the particles. Beads can be individually manipulated using their magnetic capacity and micro fluidics to transport them. In this situation, in subsequent steps sequencing ingredients can be added and washed away, according to the requirements of the specific sequencing chemistry (e.g. pyrosequencing). Herein beads are separated from each other to such extent that individual sequencing reactions can be detected.

In another alternative particular embodiment a modified version of the so-called "pyrosequencing" or "454" sequencing method (U.S. Pat. No. 7,211,390 and U.S. Pat. No. 6,956,114). In the prior art method DNA fragments are attached via a one type of linker molecule to a one type of microcarrier (see FIG. 1A). These carriers are individually distributed in emulsion droplets and arranged in wells on a substrate. The wells contain the necessary reagents and enzymes (polymerase, sulfurylase and luciferase) for the sequencing reaction and function as isolated reaction chambers. During the sequencing reaction, DNA nucleotides are added sequentially to the sample in a flow of reagents. Each time a nucleotide is incorporated, the sulfurylase and luciferase report this incorporation by emitting a light signal. The sequencing information is thus exclusively obtained from the sequencing by synthesis on the bead.

Figure 1B:
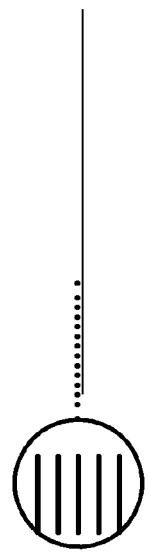

In an embodiment of the present invention, DNA fragments are attached via hybridizing capture probes on an encoded microcarrier (FIG. 1B). In this variant the sequence information obtained by the pyrosequencing technique can be combined with the sequence information of the probe by determining the code of the microbead. These codes can be determined prior to the sequencing reaction, or can be read after the sequencing reaction for those reactions only which provided an adequate sequencing signal.

Apart from polymerase dependent sequencing, the methods of the present invention can also be performed with other sequencing methods such as DNA ligase dependent annealing of oligonucleotides as described in Shendure et al. (2005) *Science* 309, 1728-1732.

Handling of Microcarriers

Depending on the sequencing methods, microcarriers are positioned on a substrate (detection region) for detection of the incorporated sequence and the identification of the encoded microcarrier, for example within miniature wells. The positioning can occur in different ways such as gravity or centrifugation, via electrical forces due to charges in the carrier or exploiting the charge of the DNA attached to the microcarrier. In a particular embodiment, the microcarriers are manipulated to a detection region using magnetic fields.

According to another embodiment, microcarriers are manipulated in a microfluidic system using pumps, electroosmosis, manipulation via electric tweezers or manipulation via magnetic fields. Detection takes place upon passage of the microcarrier in a detection cell. Optionally microcarriers are positioned and/or rotated in a magnetic and/or electric field to have the particle caged for a time sufficiently long time to perform the detection. In a particular embodiment wherein partially photobleached magnetic particles are used, these microcarriers are positioned and rotated to allow the optical detection of a code (e.g. barcode or chromophoric label) on a microcarrier.

Detection Steps

In the methods as described in the present invention, two different detection steps take place:

A first detection step comprises the identification of the code of the microcarrier (e.g. optical detection of a barcode), which provides the sequence of the capture probe which has been used to hybridize nucleic acids such as DNA from the sample and optionally has been used as a sequence primer.

The second detection step comprises the detection of the sequence of the nucleotide acid fragment that hybridized to the microcarrier.

The order of these detection steps can also be reversed.

Reversible dye terminator sequencing methods as described above generally allow determining about 30 nucleotides of a DNA molecule. When a polymorphism occurs in such a short fragment, this may be easily overlooked and become unnoticed when the sequence with the polymorphism also occurs as a wild type sequence in another part of the genome. The presence of the additional sequence obtained from the capture probe allows determination of the localization of the sequenced read on the genome, thus avoiding such problems.

In such cases wherein the determined sequence is highly similar or identical to sequences occurring at different places in the genome, the primer sequence adjacent to the determined sequence dramatically increases the information content of a DNA fragment in a sample and increases the accuracy of interpreting experimental sequencing data.

Equally, short fragments with sequencing errors may have an exact match with a sequence at another part of the genome leading to problems such as improper sequence assemblies.

Optionally, a third part of sequence information is obtained from the length of the determined sequence. Based on the position of the capture probe in the sequence and the restriction enzyme(s) used for preparing it is possible to define the length of DNA that will be generated by the DNA polymerase used to perform the sequencing. The determination of sequence length that is obtained by sequencing indicated whether the restriction site is at the predicted position. This applies when DNA is cut using restriction enzymes and the sequencing reaction continues until the end of the DNA fragment.

The methods as described in the present invention have various advantageous properties. The design of probes allows determining only the parts of interest of a sequence. The methods as described in the present invention allow a fast and reliable SNP/mutation detection and structural DNA variations such as copy number variations, and rearrangements, and avoids errors caused by repetitive sequences or pseudogenes, and errors introduced by the subsequent sequencing process. Time required for analysis of the DNA sequencing read results will be dramatically reduced because at least one part of the sequence, or even the position of the sequenced reads on the genome is already known. Furthermore, the hardware requirements to perform the data analysis are thus dramatically reduced, such that the analysis will be performed on standard personal computers.

Further advantages of the methods of the present invention are for example an enhanced speed, namely the identification of the sequence of the capture probe via reading the code is much faster than sequencing the probe itself.

Device According to the Invention

Another aspect of the present invention relates to a device for performing the above-described DNA sequencing methods. Such a device comprises a microcarrier manipulation unit, a unit for hybridizing capture probes with nucleic acids, a sequence determination unit for identifying the sequence of DNA fragment (previously) annealed to the capture probe and a unit for determining the code on a microcarrier which identifies the attached capture oligonucleotide probe.

The hybridization unit is generally a reaction chamber wherein a nucleic acid sample (typically DNA) is contacted with oligonucleotide capture probes on encoded microcarriers. This reaction chamber contains elements to change the temperature in a controlled manner for denaturing and annealing the sample. The hybridization unit optionally comprises inlets for applying or removing a nucleic acid sample, buffers, reagents, oligonucleotide capture probes. The replacement of buffers and the like can be performed by liquid wash steps or can be performed by manipulating the oligonucleotide carriers to another component of the device, such as by magnetic manipulation of the magnetic microcarrier.

According to one embodiment the hybridization unit is also used prior to the hybridization for fragmenting a DNA sample with one or more restriction enzymes.

The sequence determination unit comprises a reaction chamber, where the incorporation of nucleotides by a DNA polymerase takes place, and a detection chamber, where the identification of the incorporated nucleotides takes place. In a particular configuration of a sequencing unit the reaction and detection take place in the same chamber, for example a reaction chamber with a transparent part. Herein, microcarriers containing either one DNA fragment in the case of single molecule sequencing or alternatively carrying multiple identical fragments as the results of a carrier-based PCR-cloning step, wherein the fragments on the carrier are identical, are arranged on a surface or in wells, for the detection of incorporated nucleotide. The microcarriers are then released for a further sequencing reaction.

In another particular configuration the sequencing unit comprises a reaction chamber which is separated from the detection unit (e.g. a micro fluidics channel with a detector). After the reaction, microcarriers are manipulated into the detection unit via microfluidic manipulation, or electrical manipulation. In a particular embodiment wherein magnetic particles are used, the manipulation of the microcarriers is performed by application of a magnetic field.

The device further comprises a code determination unit. Depending of the code on the microcarrier and the nature of the incorporated nucleotide, the detection unit, which is used for determining the sequence, can be used as well for identifying the code on the microcarrier. For example, four different fluorescent markers are used for labeling the sequencing nucleotides and a fifth fluorescence marker in different intensities is used for labeling the microcarriers.

In another embodiment two different detectors are used at the same detection region, wherein the first detector determines the DNA sequence, and afterwards the second detector determines the code on the microcarrier (this sequence of events can be equally reversed).

In another embodiment, microcarriers are manipulated in a microfluidic device wherein the sequence is determined at a first position in the fluidic device by a first detector and the code on the microcarrier is determined at a second position in the fluidic device by a second detector.

The different chambers and detectors of the device are known in the art. The manipulation of magnetic particles has been described in detail, in for example US application US20080314749. Sequencing methods and devices are disclosed by e.g. Ilumina, Applied Biosystems and Roche. Methods and devices to manipulate carriers have been described for example in PCT application WO0470362.

The present invention relates to hybridization and DNA sequencing methods and devices. Use is made of information publicly available on the sequence of reference genomes, including the human genome. Methods in accordance with the present invention are applicable in any sequencing approach, but are particularly useful in the area of oncology diagnostics, and also in clinical genetics and microbiology. A highly relevant clinical application is sequencing of a selected part of a cancer genome, which contains a large number of yet unknown DNA abnormalities that are different for each tumor sequenced, like for example single or multiple nucleotide mutations, deletions and amplifications, inversions, and chromosomal rearrangements. This cannot be done by sequencing by hybridization on an array in which case with every single capture probe one nucleotide of one sequence read can be determined and the exact complementarity between capture probe and captured DNA fragment is crucial (no mismatches allowed) to enable assembly of one sequencing read; in the case of the above-mentioned cancer sequencing too many permutations in the capture probes are required to enable sequencing of sufficient parts of the tumor genome. In the invention described here, the capture probes are long enough as to allow binding of DNA fragments that contain one or more mismatches, while subsequently an unknown part, comprising at least 2 nucleotides, of the sequence of the captured fragment is sequenced, starting at the first nucleotide 5' of the hybridized part of the captured fragment. This enables sequencing of multiple unknown mutations. However in addition to this application, the invention can also be used other diagnostic applications, for example for sequencing (large) parts of the genome for the purpose of clinical genetics or for pathogen sequencing. The invention is especially suited for sequencing a selection of fragments from the whole genome of cells isolated from a biological sample, like for example a cancer biopsy. In contrast sequencing by hybridization on array is suited for sequencing one or at maximum a limited number of defined PCR products, and not DNA fragments obtained from fragmenting the whole genome.

Other arrangements of the systems and methods embodying the invention will be obvious for those skilled in the art.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A method for determining the sequence of a target nucleic acid molecule, comprising:
   providing two capture oligonucleotide probes with different sequences, each capture oligonucleotide probe including a 5' and a 3' end and one of a plurality of differently encoded microcarriers attached to the 5' end, wherein the encoded microcarrier attached to each capture oligonucleotide probe includes a code corresponding with the sequence of the capture oligonucleotide probe and its location on a reference genome which is known;
   hybridizing the capture oligonucleotide probes with a sample comprising the target nucleic acid molecule, wherein the target nucleic acid molecule includes a 5' and a 3' end and comprises two separate regions for binding the capture oligonucleotide probes, the separate regions having sequences which are at least partially complementary to the sequences of the capture oligonucleotide probes;
   determining the sequence of the hybridized target nucleic acid molecule from the 3' end of the capture oligonucleotide probes towards the 5' end of the target nucleic acid by using the capture oligonucleotide probes as primers and generating a sequence read from each capture oligonucleotide probe of at least 2 nucleotides using a DNA polymerase;
   determining the codes on the plurality of differently encoded microcarriers;
   identifying the nucleotide sequence of the capture oligonucleotide probes corresponding with the code on the encoded microcarrier attached to the capture oligonucleotide probes and the locations of the capture oligonucleotide probes on the reference genome; and
   combining the sequence information from the target hybridized nucleic acid molecule with the sequence information from the capture oligonucleotide probes to determine the sequence of the target nucleic acid molecule.

2. The method according to claim 1, wherein the plurality of differently encoded microcarriers, the two capture oligonucleotide probes, and the sample are in an emulsion.

3. The method according to claim 2, wherein the code of the encoded carrier is determined by optical detection of a barcode.

4. The method according to claim 1, wherein the microcarrier is a magnetic particle.

5. The method according to claim 1, wherein the sequencing reaction is performed by FRET single molecule sequencing with the capture oligonucleotide probes as sequencing primers.

6. The method according to claim 1, wherein the sample includes genomic DNA fragmented with a restriction enzyme to produce the target nucleic acid molecule, the target nucleic acid molecule including at least 200 base pairs.

7. The method according to claim 1, wherein the length of each capture oligonucleotide probe is between 150 and 200 nucleotides.

8. A device for determining the sequence of a target nucleic acid sample, said device comprising a unit for annealing capture oligonucleotide probes with nucleic acids, a unit for determining the sequence of the target nucleic acid sample, a unit for manipulating a plurality of encoded microcarriers, and a unit for determining the code of one of the plurality of encoded microcarriers, wherein the device determines the sequence of the target nucleic acid sample by:
    providing two capture oligonucleotide probes with different sequences, each capture oligonucleotide probe including a 5' and a 3' end and one of the plurality of differently encoded microcarriers attached to the 5' end, wherein the encoded microcarrier attached to each capture oligonucleotide probe includes a code corresponding with the sequence of the capture oligonucleotide probe and its location on a reference genome which is known;
    hybridizing the capture oligonucleotide probes with a sample comprising the target nucleic acid molecule, wherein the target nucleic acid molecule includes a 5' and a 3' end and comprises two separate regions for binding the capture oligonucleotide probes, the separate regions having sequences which are at least partially complementary to the sequences of the capture oligonucleotide probes;
    determining the sequence of the hybridized target nucleic acid molecule from the 3' end of the capture oligonucleotide probes towards the 5' end of the target nucleic acid by using the capture oligonucleotide probes as primers and generating a sequence read from each capture oligonucleotide probe of at least 2 nucleotides using a DNA polymerase;
    determining the codes on the plurality of differently encoded microcarriers;
    identifying the nucleotide sequence of the capture oligonucleotide probes corresponding with the code on the encoded microcarrier attached to the capture oligonucleotide probes and the locations of the capture oligonucleotide probes on the reference genome; and
    combining the sequence information from the target hybridized nucleic acid molecule with the sequence information from the capture oligonucleotide probes to determine the sequence of the target nucleic acid molecule.

9. The device according to claim 8 is a microfluidic device.

10. The device according to claim 8, wherein the unit for manipulating the plurality of encoded microcarriers applies at least one magnetic field.

11. A method for determining the sequence of a whole genome DNA fragment, comprising:
    cleaving a whole genome into first and second DNA fragments having a 5' and 3' end with at least one restriction enzyme at restriction points;
    determining a first binding region on the first DNA fragment for annealing with a first capture oligonucleotide probe having a 5' and 3' end;
    annealing the first capture oligonucleotide probe with an attached first encoded microcarrier to the first region, wherein the first encoded microcarrier identifies the sequence of the first capture oligonucleotide probe and its location on the whole genome which is known;
    determining the sequence of the annealed first DNA fragment from the 3' end of the first capture oligonucleotide probe towards the 5' end of the annealed first DNA fragment by using the first capture oligonucleotide probe as a first primer and by generating a sequence read of at least 2 nucleotides using a DNA polymerase;
    determining the code on the first encoded microcarrier;
    identifying the nucleotide sequence of the first capture oligonucleotide probe corresponding with the code on the first encoded microcarrier and its location on the whole genome;
    combining the sequence read information obtained from using the first primer with the sequence information from the first capture oligonucleotide probe to determine the sequence of the first DNA fragment;
    determining a second binding region for binding a second capture oligonucleotide probe onto the first DNA fragment; and
    annealing the second capture oligonucleotide probe with an attached second encoded microcarrier to the second binding region, wherein the encoded microcarrier identifies the sequence of the second capture oligonucleotide probe and its location on the whole genome.

12. The method according to claim 11, wherein the first DNA fragment is between 200 and 1000 base pairs.

13. The method according to claim 11, wherein the first oligonucleotide probe is between 150 and 200 nucleotides.

14. The method according to claim 11, wherein determining the first binding region includes determining a sequence location on the first DNA fragment at least nucleotides 2 nucleotides away from the 5' end of the first DNA fragment.

15. The method according to claim 11, further including:
    determining the sequence of the annealed first DNA fragment from the 3' end of the second capture oligonucleotide probe towards the 5' end of the first DNA fragment by using the second capture oligonucleotide probe as a second primer and generating a sequence read of at least 2 nucleotides using a DNA polymerase;
    determining the code on the second encoded microcarrier;
    identifying the nucleotide sequence of the second capture oligonucleotide probe corresponding with the code on the second encoded microcarrier and its location on the whole genome; and
    combining the sequence read information obtained from using the first and second primers with the sequence information from the first and second capture oligonucleotide probes to determine the sequence of the first DNA fragment.

16. The method according to claim 11, further including altering a spacing on the first DNA fragment between the first and second regions based on how the sequence read is generated.

* * * * *